(12) United States Patent  
Walter et al.

(10) Patent No.: US 7,514,584 B2
(45) Date of Patent: Apr. 7, 2009

(54) PROCESS FOR THE PRODUCTION OF 2(2-AMINOPHENYL)-BICYLOPROPANE DERIVATIVES

(75) Inventors: Harald Walter, Basel (CH); Camilla Corsi, Basel (CH); Josef Ehrenfreund, Basel (CH); Clemens Lamberth, Basel (CH); Hermann Schneider, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 11/815,895

(22) PCT Filed: Feb. 20, 2006

(86) PCT No.: PCT/EP2006/001508

§ 371 (c)(1),
(2), (4) Date: Aug. 9, 2007

(87) PCT Pub. No.: WO2006/087223

PCT Pub. Date: Aug. 24, 2006

(65) Prior Publication Data

US 2008/0161610 A1    Jul. 3, 2008

(30) Foreign Application Priority Data

Feb. 21, 2005   (CH) .................... 0302/05

(51) Int. Cl.
 *C07C 211/00* (2006.01)
 *C07C 205/00* (2006.01)
(52) U.S. Cl. ...................... 564/307; 568/928
(58) Field of Classification Search ............ None
 See application file for complete search history.

(56) References Cited

FOREIGN PATENT DOCUMENTS

WO  03074491  9/2003

WO  2006015865  2/2006

*Primary Examiner*—Paul A Zucker
(74) *Attorney, Agent, or Firm*—Thomas Hamilton

(57) ABSTRACT

The present invention relates to a process for the preparation of compounds of formula (I) wherein the substituents are as defined in claim 1, by a) reaction of a compound of formula (II) to form a compound of formula (III) b) reaction of that compound in the presence of a base to form a compound of formula (IV) c) conversion of that compound in the presence of a reducing agent into a compound of formula (I).

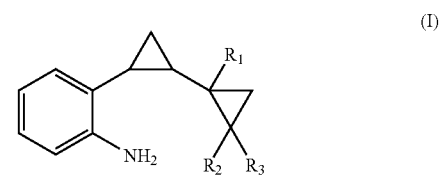

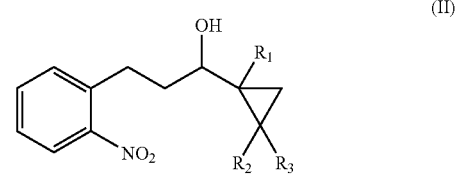

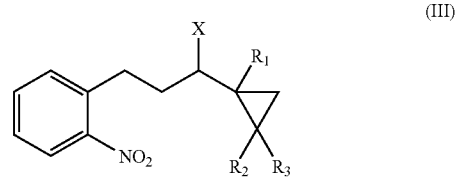

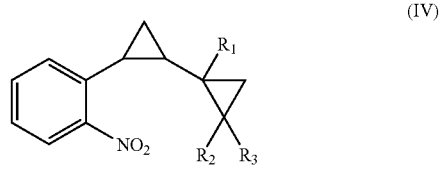

3 Claims, No Drawings

PROCESS FOR THE PRODUCTION OF 2(2-AMINOPHENYL)-BICYLOPROPANE DERIVATIVES

This application is a 371 of International Application No. PCT/EP2006/001508 filed Feb. 20, 2006, which claims priority to CH-0302/05 filed Feb. 21, 2005, the contents of which are incorporated herein by reference.

The present invention relates to a process for the preparation of 2-(2-aminophenyl)-bicyclopropanes, and to novel nitrobenzene intermediates for use in that process.

2-(2-Aminophenyl)-bicyclopropanes, such as, for example, unsubstituted 2-(2-aminophenyl)-bicyclopropane, are valuable intermediates for the preparation of ortho-bicyclopropylcarboxanilide fungicides, such as are described, for example, in WO 03/074491.

In WO 03/074491, a process for the preparation of 2-(2-aminophenyl)-bicyclopropanes is described (see Scheme 1):

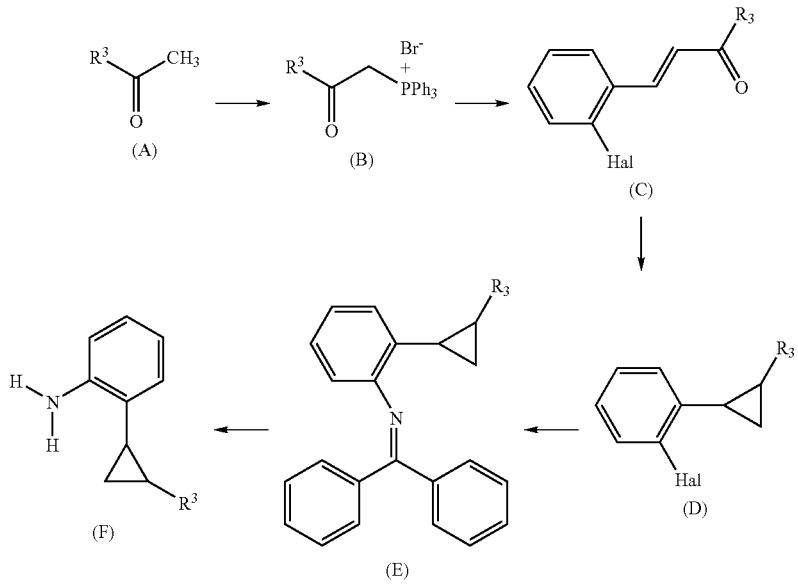

Scheme 1:

According to WO 03/074491, ketones of formula (A), wherein $R^3$ may be, inter alia, unsubstituted or substituted cyclopropyl, are reacted, for example, first with bromine and methanol and then with triphenylphosphine. The compounds of formula (B) obtained are converted in a two-step reaction into compounds of formula (C) wherein Hal is bromine or iodine (first, reaction with sodium hydride, then reaction with 2-bromobenzaldehyde or 2-iodobenzaldehyde, respectively). Compounds of formula (C) can be converted into the corresponding 2-(2-halophenyl)-bicyclopropanes (D) by Kishner cyclisation, which proceeds by way of a $\Delta^2$-pyrazoline. For that purpose, compounds of formula (C) are reacted, with heating, with hydrazine, as a result of which the corresponding $\Delta^2$-pyrazolines are formed. Subsequently, potassium hydroxide is added for isomerisation, and renewed heating is carried out to remove $N_2$. 2-(2-Halophenyl)-bicyclopropanes (D) can be aminated in a two-step reaction to form the corresponding 2-(2-aminophenyl)-bicyclopropanes (F). For that purpose, first of all benzophenone imine, sodium tert-butanolate, tris(dibenzylideneacetone)-dipalladium ($Pd_2dba_3$) and racemic 2,2'-bis(diphenylphosphine)-1,1'-binaphthyl (BINAP) are added. The resulting imines (E) are reacted in the second reaction step, for example with hydroxylamine and sodium acetate, to form the corresponding 2-(2-aminophenyl)-bicyclopropanes (F).

Such a reaction procedure is not suitable, however, for the preparation of 2-(2-aminophenyl)-bicyclopropanes, especially for large-scale preparation processes, because of the costly palladium-containing catalysts and ligands, such as, for example, BINAP.

In WO 03/074491, two further routes for the preparation of 2-(2-aminophenyl)-bicyclopropanes are described. A first route is by way of nitration of bicyclopropyl-benzenes. It has been found, however, that the reaction is not workable in view of the fact that the cyclopropyl ring linked directly to the benzene ring has increased reactivity in bicyclopropyl-benzenes with respect to electrophiles. A second route is by way of application of the Simmons-Smith reaction ($Zn/Cu$, $CH_2I_2$ with ether as solvent) to 1-((E/Z)-2-cyclopropylvinyl)-2-nitrobenzenes. In that case, too, the reaction has been found to be unsuitable for the preparation of 2-(2-nitrophenyl)-bicyclopropanes, since the reactivity of the double bond is too low.

The aim of the present invention is therefore to provide a process for the preparation of 2-(2-aminophenyl)-bicyclopropanes that allows such compounds to be prepared in an economically advantageous manner in high yields and in good quality.

The present invention accordingly relates to a process for the preparation of compounds of formula I

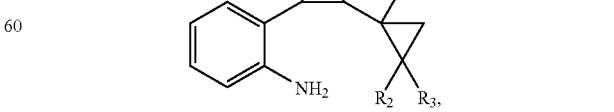

(I)

wherein $R_1$, $R_2$ and $R_3$ are each independently of the others hydrogen or methyl, which comprises a) reaction of a compound of formula II

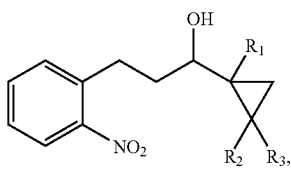
(II)

wherein $R_1$, $R_2$ and $R_3$ are as defined for formula I, either a1) with triphenylphosphine dibromide or triphenylphosphine dichloride or a2) with $RSO_2Cl$, wherein R is $C_1$-$C_4$alkyl, $C_1$-$C_4$fluoroalkyl, benzyl, phenyl, nitrophenyl, halophenyl or $C_1$-$C_6$alkylphenyl, in the presence of a base, to form a compound of formula III

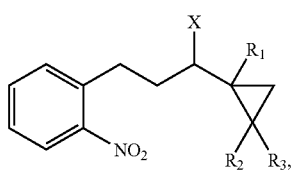
(III)

wherein X is bromine, chlorine or $OSO_2R$, wherein R is $C_1$-$C_4$alkyl, $C_1$-$C_4$fluoroalkyl, benzyl, phenyl, nitrophenyl, halophenyl or $C_1$-$C_6$alkylphenyl, and $R_1$, $R_2$ and $R_3$ are as defined for formula I; and b) reaction of that compound in the presence of a base to form a compound of formula IV

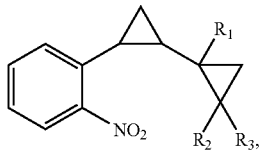
(IV)

wherein $R_1$, $R_2$ and $R_3$ are as defined for formula 1; and c) conversion of that compound in the presence of a reducing agent into a compound of formula I.

Ortho-bicyclopropylcarboxanilide fungicides are generally chiral molecules that occur in isomeric forms. Accordingly they exist as trans/cis isomers based on the substitution pattern of the cyclopropyl ring linked directly to the benzene ring. It is known that the fungicidal activity of compounds such as are described, for example, in WO 03/074491, can be influenced by the stereochemistry. It has been found in the case of the ortho-bicyclopropylcarboxanilide fungicides described therein that the trans isomers generally have higher fungicidal activity. The development of a process that enables the production of a marked excess of trans ortho-bicyclopropylcarboxanilide fungicides is therefore extremely desirable.

The reaction sequence described in WO 03/074491 (Scheme 1) yields a trans:cis ratio of the 2-(2-aminophenyl)-bicyclopropane isomers of about 2:1.

A further aim of the present invention is accordingly to provide a process for the preparation of 2-(2-aminophenyl)-bicyclopropanes having a significantly higher proportion of trans isomers.

The process according to the invention allows compounds of formula I

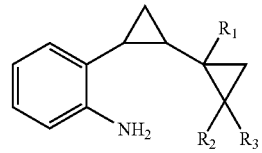
(I)

to be produced wherein $R_1$, $R_2$ and $R_3$ are each independently of the others hydrogen or methyl and wherein the ratio of compounds of formula Ia (trans)

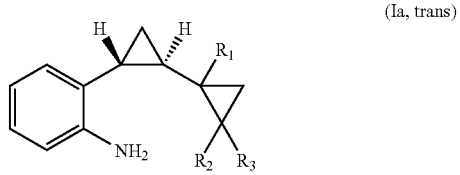
(Ia, trans)

to compounds of formula Ib (cis)

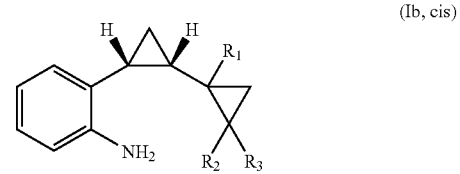
(Ib, cis)

is more than 2:1.

The alkyl groups in the definitions of the substituents may be straight-chain or branched and are, for example, methyl, ethyl, n-propyl, isopropyl, n-butyl, sec-butyl, isobutyl, tert-butyl, pentyl and hexyl and branched isomers thereof.

Halogen in the context of halophenyl is generally fluorine, chlorine, bromine or iodine.

Fluoroalkyl groups having a chain length of from 1 to 4 carbon atoms are, for example, fluoromethyl, difluoromethyl, trifluoromethyl, 2,2,2-trifluoroethyl, 1-fluoroethyl, 2-fluoroethyl, 2-fluoroprop-2-yl, pentafluoroethyl, 2,2,3,3-tetrafluoroethyl, pentafluoroethyl or heptafluoro-n-propyl; fluoroalkyl groups are preferably trichloromethyl, fluoromethyl, dichlorofluoromethyl, difluoromethyl, trifluoromethyl, pentafluoroethyl or heptafluoro-n-propyl.

Compounds of formula I occur in various stereoisomeric forms, which are represented by formulae $I_I$, $I_{II}$, $I_{III}$, and $I_{IV}$:

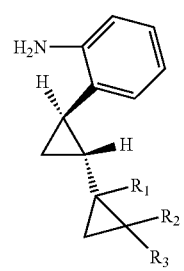
$I_I$

-continued

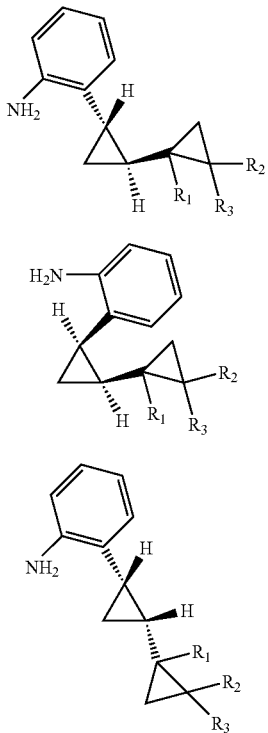

The process according to the invention includes the preparation of those stereoisomeric forms of formulae $I_I$, $I_{II}$, $I_{III}$, and $I_{IV}$, wherein $R_1$, $R_2$ and $R_3$ are as defined for formula I, and the preparation of mixtures of those stereoisomeric forms in any ratio.

In the context of the present invention, compounds of formula Ia (trans)

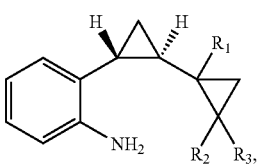
(Ia, trans)

wherein $R_1$, $R_2$ and $R_3$ are as defined for formula I, are understood to be compounds of formula $I_I$, wherein $R_1$, $R_2$ and $R_3$ are as defined for formula $I_{II}$; compounds of formula $I_{II}$, wherein $R_1$, $R_2$ and $R_3$ are as defined for formula I; or a mixture, in any ratio, of compounds of formula $I_I$, wherein $R_1$, $R_2$ and $R_3$ are as defined for formula I, and compounds of formula $I_{II}$, wherein $R_1$, $R_2$ and $R_3$ are as defined for formula I.

In the context of the present invention, compounds of formula Ia (trans)

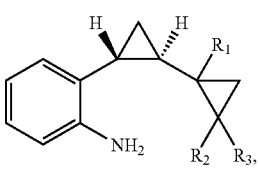
(Ia, trans)

wherein $R_1$, $R_2$ and $R_3$ are as defined for formula I, are understood to be, preferably, a racemic mixture of compounds of formula $I_I$, wherein $R_1$, $R_2$ and $R_3$ are as defined for formula I, and compounds of formula $I_{II}$, wherein $R_1$, $R_2$ and $R_3$ are as defined for formula I.

In the context of the present invention, compounds of formula Ib (cis)

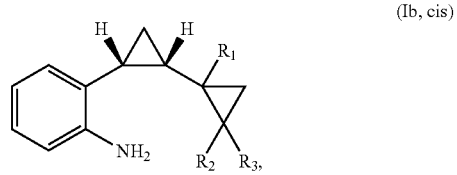
(Ib, cis)

wherein $R_1$, $R_2$ and $R_3$ are as defined for formula I, are understood to be compounds of formula $I_{III}$, wherein $R_1$, $R_2$ and $R_3$ are as defined for formula I; compounds of formula $I_{IV}$, wherein $R_1$, $R_2$ and $R_3$ are as defined for formula I; or a mixture, in any ratio, of compounds of formula $I_{III}$, wherein $R_1$, $R_2$ and $R_3$ are as defined for formula I, and compounds of formula $I_{IV}$, wherein $R_1$, $R_2$ and $R_3$ are as defined for formula I.

In the context of the present invention, compounds of formula Ib (cis)

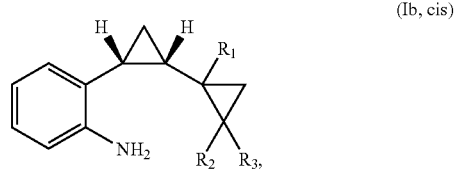
(Ib, cis)

wherein $R_1$, $R_2$ and $R_3$ are as defined for formula I, are understood to be, preferably, a racemic mixture of compounds of formula $I_{III}$, wherein $R_1$, $R_2$ and $R_3$ are as defined for formula I, and compounds of formula $I_{IV}$, wherein $R_1$, $R_2$ and $R_3$ are as defined for formula I.

Compounds of formula IV occur in various stereoisomeric forms, which are represented by formulae $IV_I$, $IV_{II}$, $IV_{III}$ and $IV_{IV}$:

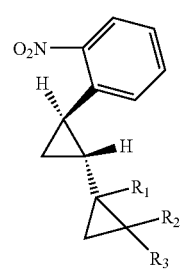
$IV_I$

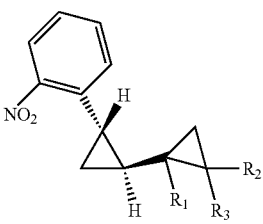
$IV_{II}$

-continued

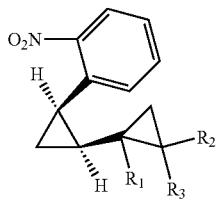
(IV$_{III}$)

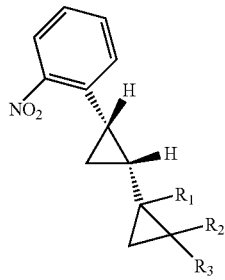
(IV$_{IV}$)

The process according to the invention includes the preparation of those stereoisomeric forms of formulae IV$_I$, IV$_{II}$, IV$_{III}$ and IV$_{IV}$, wherein R$_1$, R$_2$ and R$_3$ are as defined for formula I, and the preparation of mixtures of those stereoisomeric forms in any ratio.

In the context of the present invention, compounds of formula IVa (trans)

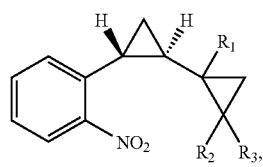
(IVa, trans)

wherein R$_1$, R$_2$ and R$_3$ are as defined for formula I, are understood to be compounds of formula IV$_I$, wherein R$_1$, R$_2$ and R$_3$ are as defined for formula I; compounds of formula IV$_{II}$, wherein R$_1$, R$_2$ and R$_3$ are as defined for formula I; or a mixture, in any ratio, of compounds of formula IV$_I$, wherein R$_1$, R$_2$ and R$_3$ are as defined for formula I, and compounds of formula IV$_{II}$, wherein R$_1$, R$_2$ and R$_3$ are as defined for formula I.

In the context of the present invention, compounds of formula IVa (trans)

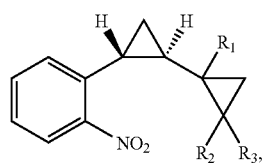
(IVa, trans)

wherein R$_1$, R$_2$ and R$_3$ are as defined for formula I, are understood to be, preferably, a racemic mixture of compounds of formula IV$_I$, wherein R$_1$, R$_2$ and R$_3$ are as defined for formula I, and compounds of formula IV$_{II}$, wherein R$_1$, R$_2$ and R$_3$ are as defined for formula I.

In the context of the present invention, compounds of formula IVb (cis)

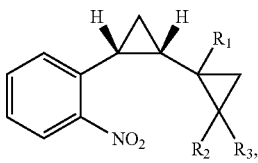
(IVb, cis)

wherein R$_1$, R$_2$ and R$_3$ are as defined for formula I, are understood to be compounds of formula IV$_{III}$, wherein R$_1$, R$_2$ and R$_3$ are as defined for formula I; compounds of formula IV$_{IV}$, wherein R$_1$, R$_2$ and R$_3$ are as defined for formula I; or a mixture, in any ratio, of compounds of formula IV$_{III}$, wherein R$_1$, R$_2$ and R$_3$ are as defined for formula I, and compounds of formula IV$_{IV}$, wherein R$_1$, R$_2$ and R$_3$ are as defined for formula I.

In the context of the present invention, compounds of formula IVb (cis)

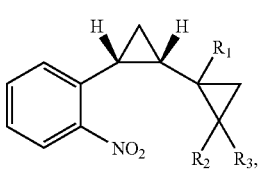
(IVb, cis)

wherein R$_1$, R$_2$ and R$_3$ are as defined for formula I, are understood to be, preferably, a racemic mixture of compounds of formula IV$_{III}$, wherein R$_1$, R$_2$ and R$_3$ are as defined for formula I, and compounds of formula IV$_{IV}$, wherein R$_1$, R$_2$ and R$_3$ are as defined for formula I.

In the context of the present invention, a "racemic mixture" of two enantiomers is understood to be a mixture of the two enantiomers in a ratio substantially equal to 1:1.

The process according to the invention is suitable especially for the preparation of compounds of formula I wherein R$_2$ and R$_3$ are hydrogen.

The process according to the invention is suitable more especially for the preparation of compounds of formula I wherein R$_1$, R$_2$ and R$_3$ are hydrogen.

The process according to the invention is suitable more especially for the preparation of compounds of formula I wherein R$_1$ is methyl and R$_2$ and R$_3$ are hydrogen.

Process Step a):

In an embodiment (a1) of the process according to the invention, in Process Step a), a compound of formula II is reacted with triphenylphosphine dibromide or triphenylphosphine dichloride.

In that embodiment, either triphenylphosphine dibromide or triphenylphosphine dichloride is added directly to the compounds of formula II, or triphenylphosphine dibromide or triphenylphosphine dichloride is generated in situ in the reaction mixture by the addition of bromine or chlorine in the presence of triphenylphosphane.

Suitable amounts of triphenylphosphine dibromide or triphenylphosphine dichloride for that reaction are, for example, from 1 to 3 equivalents, especially from 1 to 1.5 equivalents.

When triphenylphosphine dibromide or triphenylphosphine dichloride is generated in situ, an amount, for example, of from 1 to 3 equivalents, especially from 1 to 1.5 equivalents, of bromine or chlorine is suitable. Suitable amounts of triphenylphosphane for that variant of the reaction are, for example, from 1 to 3 equivalents, especially from 1 to 1.5 equivalents.

In that embodiment, the reaction can be carried out in the presence of an inert solvent. Suitable solvents are, for example, ethers, for example tetrahydrofuran or dioxane, or $CH_3CN$, and mixtures thereof; $CH_3CN$ is preferred.

Temperatures are generally from –20° C. to 80° C., with a range from –20° C. to 25° C. being preferred; special preference is given to carrying out the reaction at ambient temperature. The reaction time for that reaction is generally from 1 to 48 hours, preferably from 1 to 18 hours.

In a further embodiment (a2) of the process according to the invention, in Process Step a), a compound of formula II is reacted in the presence of a base with $RSO_2Cl$, wherein R is $C_1$-$C_4$alkyl, $C_1$-$C_4$fluoroalkyl, benzyl, phenyl, nitrophenyl, halophenyl or $C_1$-$C_6$alkylphenyl, especially $C_1$-$C_4$alkyl, more especially methyl.

For that reaction, suitable amounts of $RSO_2Cl$, wherein R is $C_1$-$C_4$alkyl, $C_1$-$C_4$fluoroalkyl, benzyl, phenyl, nitrophenyl, halophenyl or $C_1$-$C_6$alkylphenyl, are, for example, from 1 to 3 equivalents, especially from 1 to 1.2 equivalents.

Suitable bases are, for example, tertiary amines, such as trialkylamines, e.g. trimethylamine, triethylamine, diisopropylethylamine (Hünig's base), tri-n-butylamine, N,N-dimethylaniline or N-methylmorpholine, or inorganic bases, such as carbonates, e.g. $K_2CO_3$ or $Na_2CO_3$, or hydroxides, e.g. NaOH or KOH, with preference being given to trialkylamines and special preference being given to triethylamine.

Suitable amounts of base for that reaction are, for example, from 1 to 3 equivalents, especially from 1 to 1.3 equivalents.

The reaction is preferably carried out in the presence of an inert solvent. Suitable solvents are, for example, dichloromethane, pyridine or ethers, for example tetrahydrofuran, and mixtures thereof, with preference being given to dichloromethane or pyridine, and special preference being given to dichloromethane.

Temperatures are generally from –20° C. to 80° C., with a range from –20° C. to 25° C. being preferred; special preference is given to carrying out the reaction at ambient temperature.

The reaction time for that reaction is generally from 1 to 48 hours, preferably from 1 to 18 hours.

The starting compounds of formula II, wherein $R_1$, $R_2$ and $R_3$ are as defined for formula I, can be prepared, for example, in accordance with the following reaction sequence (see Scheme 2):

Scheme 2:

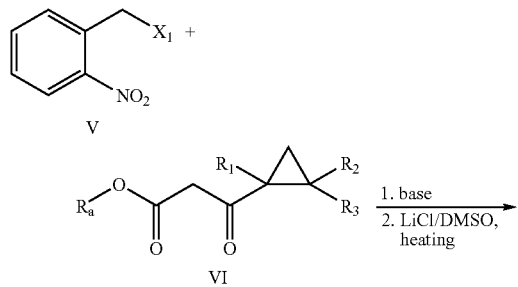

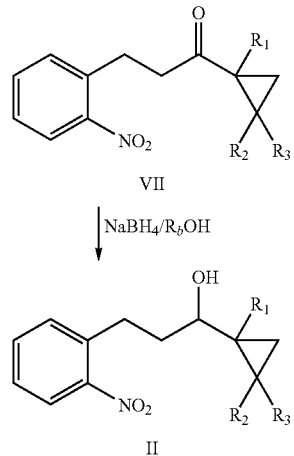

Compounds of formula V, wherein $X_1$ is chlorine or bromine, are reacted with compounds of formula VI, wherein $R_1$, $R_2$ and $R_3$ are as defined for formula I and $R_a$ is $C_1$-$C_6$alkyl, in a two-step reaction sequence to form compounds of formula VII, wherein $R_1$, $R_2$ and $R_3$ are as defined for formula I. In the first reaction step, compounds of formula V are reacted with compounds of formula VI under basic conditions, for example obtained by addition of NaH, NaOH or $K_2CO_3$. After isolation of the crude product, heating in dimethyl sulfoxide (DMSO) in the presence of LiCl is carried out in the second reaction step. The resulting compounds of formula VII can be reacted to form compounds of formula II by addition of sodium borohydride in a protic solvent $R_bOH$, wherein $R_b$ is $C_1$-$C_6$alkyl, such as, for example, isopropanol.

Compounds of formula V, wherein $X_1$ is chlorine or bromine, are known and are obtainable commercially.

Some of the compounds of formula VI, wherein $R_1$, $R_2$ and $R_3$ are as defined for formula I and $R_a$ is $C_1$-$C_6$alkyl, are known and are obtainable commercially. The remaining compounds of formula VI, wherein $R_1$, $R_2$ and $R_3$ are as defined for formula I and $R_a$ is $C_1$-$C_6$alkyl, can be prepared in an analogous manner to preparation processes such as are described, for example, in Journal of Organic Chemistry 68(1), 27-34 (2003) and in Organic Preparations and Procedures International 10(5), 221-224 (1978).

Process Step b):

Suitable bases for Process Step b) are, for example, nitrogen-containing organic bases, such as, for example, tertiary amines, such as trialkylamines, e.g. trimethylamine, triethylamine, diisopropylethylamine (Hünig's Base), or tri-n-butylamine, N,N-dimethylaniline or N-methyl-morpholine, piperidine, pyrrolidine, alkali metal or alkaline earth metal alcoholates, such as, for example, lithium, sodium or potassium alcoholates, especially methanolates, ethanolates or butanolates, or inorganic bases, such as hydroxides, e.g. NaOH or KOH, or hydrides, such as, for example, NaH.

Bases to which preference is given are hydroxides, especially KOH, hydrides, especially NaH, or alkali metal alcoholates, especially potassium tert-butanolate.

Suitable amounts of base for that reaction are, for example, from 1 to 3 equivalents, especially from 1.1 to 1.8 equivalents.

The reaction is preferably carried out in the presence of an inert solvent. Suitable solvents are, for example, alcohols, such as methanol, ethanol, propanol or isopropanol, or aprotic solvents, such as tetrahydrofuran, dimethylformamide, dimethylacetamide, N-methyl-pyrrolidone or dimethyl sulfoxide, and also mixtures thereof; dimethyl sulfoxide or dimethylformamide is especially preferred.

Temperatures are generally from 0° C. to 80° C., with a range from 0° C. to 25° C. being preferred; special preference is given to carrying out the reaction at ambient temperature.

The reaction time for that reaction is generally from 1 to 48 hours, preferably from 1 to 18 hours.

Process Step c):

A suitable reducing agent for Process Step c) is, for example, hydrogen in the presence of a metal catalyst.

Suitable amounts of reducing agent for that reaction are, for example, from 1 to 5 equivalents, especially from 1 to 1.3 equivalents.

Suitable metal catalysts are, for example, platinum catalysts, such as, for example, platinum-carbon catalysts; palladium catalysts or rhodium catalysts, with special preference being given to platinum catalysts.

Suitable amounts of metal catalyst for that reaction are, for example, from 0.001 to 0.5 equivalent, especially from 0.01 to 0.1 equivalent.

The reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, dioxane or toluene, and mixtures thereof. Special preference is given to ethanol or methanol.

Temperatures are generally from 0° C. to 80° C., with a range from 0° C. to 25° C. being preferred; special preference is given to carrying out the reaction at ambient temperature.

The reaction time for that reaction is generally from 1 to 48 hours, preferably from 1 to 6 hours.

By selecting suitable reaction conditions, the compound of formula III obtained in Reaction Step a) can be reacted to form a compound of formula IV directly, without isolation of intermediates. That reaction procedure is a particular advantage of the process according to the invention.

The process according to the invention is suitable for the preparation of compounds of formula I, wherein $R_1$, $R_2$ and $R_3$ are each independently of the others hydrogen or methyl, very especially by a) reaction of a compound of formula II, wherein $R_1$, $R_2$ and $R_3$ are each independently of the others hydrogen or methyl, with $RSO_2Cl$, wherein R is $C_1$-$C_4$alkyl, in the presence of triethylamine in a temperature range of from −20° C. to 25° C., using dichloromethane as solvent, to form a compound of formula III, wherein X is $OSO_2$—$C_1$-$C_4$alkyl and $R_1$, $R_2$ and $R_3$ are as defined for formula I; and b) reaction of that compound in the presence of a base selected from KOH, NaH and potassium tert-butanolate, in a temperature range of from −20° C. to 25° C., using a solvent selected from dimethyl sulfoxide and dimethylformamide, to form a compound of formula IV, wherein $R_1$, $R_2$ and $R_3$ are as defined for formula I; and c) conversion of that compound into a compound of formula I in the presence of hydrogen and a platinum catalyst, in a temperature range from 0° C. to 25° C., using ethanol as solvent.

For that preferred embodiment there are especially suitable compounds of formula I wherein $R_2$ and $R_3$ are hydrogen.

For that preferred embodiment there are very especially suitable compounds of formula I wherein $R_1$, $R_2$ and $R_3$ are hydrogen.

The present invention is explained in greater detail by way of the following Examples:

EXAMPLE P1

Preparation of 2-(2-nitrophenyl)-bicyclopropane

A mixture of 0.5 g of 1-cyclopropyl-3-(2-nitrophenyl)-propan-1-ol (2.26 mmol), 0.26 g of triethylamine (2.6 mmol) and 12 ml of dichloromethane is cooled to a temperature of 5° C. and 0.28 g of methanesulfonic acid chloride, dissolved in 3 ml of dichloromethane, is added dropwise. The resulting mixture is stirred for 16 hours at ambient temperature. The organic phase is washed with ice-water and dried over sodium sulfate and concentrated by evaporation. 1-Cyclopropyl-3-(2-nitrophenyl)-propyl methanesulfonate is obtained in the form of a crude product, which is used directly in the cyclisation.

The 1-cyclopropyl-3-(2-nitrophenyl)-propyl methanesulfonate is dissolved in 15 ml of dimethyl sulfoxide and 0.17 g of potassium hydroxide (2.48 mmol) is added, and stirring is carried out for 5 hours at ambient temperature. The reaction mixture is added to ice-water. Extraction is carried out with ethyl acetate and the organic phase is dried over sodium sulfate and concentrated by evaporation. Chromatography on silica gel is carried out in order to remove by-products (eluant: ethyl acetate/hexane 1:15). After removal of the eluant, 0.28 g of 2-(2-nitrophenyl)-bicyclopropane (61% of theory) is obtained in the form of a brownish liquid (trans:cis ratio: 4.5:1). $^1$H-NMR of trans-2-(2-nitrophenyl)-bicyclopropane ($CDCl_3$-ppm): 0.17/m/1H, 0.19/m/1H, 0.42/m/1H, 0.48/m/1H, 0.83/m/1H, 0.84/m/1H, 0.99/m/1H, 1.13/m/1H, 2.17/m/1H, 7.10/dd/1H, 7.25/m/1H, 7.45/m/1H, 7.78/dd/1H); $^1$H-NMR of cis-2-(2-nitrophenyl)-bicyclopropane ($CDCl_3$-ppm): −0.09/m/1H, 0.02/m/1H, 0.06/m/1H, 0.27/m/1H, 0.71/m/1H, 0.85/m/1H, 0.98/m/1H, 1.10/m/1H, 2.53/m/1H, 7.35/m/1H, 7.45/m/1H, 7.52/m/1H, 7.92/dd/1H.

EXAMPLE P2

Preparation of 2-(2-nitrophenyl)-bicyclopropane

A mixture of 0.5 g of 1-cyclopropyl-3-(2-nitrophenyl)-propan-1-ol (2.26 mmol), 0.26 g of triethylamine (2.6 mmol) and 12 ml of dichloromethane is cooled to a temperature of 5° C. and 0.28 g of methanesulfonic acid chloride, dissolved in 3 ml of dichloromethane, is added dropwise. The resulting mixture is stirred for 16 hours at ambient temperature. The organic phase is washed with ice-water and dried over sodium sulfate and concentrated by evaporation. 1-Cyclopropyl-3-(2-nitrophenyl)-propyl methanesulfonate is obtained in the form of a crude product, which is used directly in the cyclisation.

The 1-cyclopropyl-3-(2-nitrophenyl)-propyl methanesulfonate is dissolved in 15 ml of dimethylformamide and 0.21 g of potassium hydroxide (3.2 mmol) is added, and stirring is carried out for 6 hours at ambient temperature. The reaction mixture is added to ice-water. Extraction is carried out with ethyl acetate, and the organic phase is dried over sodium sulfate and concentrated by evaporation. Chromatography on silica gel is carried out in order to remove by-products (eluant: ethyl acetate/hexane 1:15). After removal of the eluant, 0.28 g of 2-(2-nitrophenyl)-bicyclopropane (61% of theory) is obtained in the form of a brownish liquid (trans:cis ratio: 4.4:1).

EXAMPLE P3

Preparation of 2-(2-nitrophenyl)-bicyclopropane

A mixture of 2.21 g of 1-cyclopropyl-3-(2-nitrophenyl)-propan-1-ol (10 mmol), 1.21 g of triethylamine (12 mmol) and 20 ml of dichloromethane is cooled to a temperature of 5° C. and 1.26 g of methanesulfonic acid chloride (11 mmol), dissolved in 5 ml of dichloromethane, are added dropwise. The resulting mixture is stirred for 16 hours at ambient temperature. The organic phase is washed with ice-water and dried over sodium sulfate and concentrated by evaporation. 1-Cyclopropyl-3-(2-nitrophenyl)-propyl methanesulfonate is obtained in the form of a crude product, which is used directly in the cyclisation.

0.48 g of sodium hydride (12 mmol) is introduced into 10 ml of dimethyl sulfoxide and a solution consisting of the 1-cyclopropyl-3-(2-nitrophenyl)-propyl methanesulfonate and 15 ml of DMSO is added. Stirring is then carried out for 5 hours at ambient temperature. The reaction mixture is added to ice-water. Extraction is carried out with ethyl acetate, and the organic phase is dried over sodium sulfate and concentrated by evaporation. Chromatography on silica gel is carried out in order to remove by-products (eluant: ethyl acetate/hexane 1:15). After removal of the eluant, 0.28 g of 2-(2-nitrophenyl)-bicyclopropane (64% of theory) is obtained in the form of a brownish liquid (trans:cis ratio: 4.1:1).

EXAMPLE P4

Preparation of 2-(2-nitrophenyl)-bicyclopropane

A mixture of 0.5 g of 1-cyclopropyl-3-(2-nitrophenyl)-propan-1-ol (2.26 mmol), 0.26 g of triethylamine (2.6 mmol) and 12 ml of dichloromethane is cooled to a temperature of 5° C. and 0.28 g of methanesulfonic acid chloride, dissolved in 3 ml of dichloromethane, is added dropwise. The resulting mixture is stirred for 16 hours at ambient temperature. The organic phase is washed with ice-water and dried over sodium sulfate and concentrated by evaporation. 1-Cyclopropyl-3-(2-nitrophenyl)-propyl methanesulfonate is obtained in the form of a crude product, which is used directly in the cyclisation.

The 1-cyclopropyl-3-(2-nitrophenyl)-propyl methanesulfonate is dissolved in 15 ml of dimethyl sulfoxide and 0.28 g of potassium tert-butanolate (2.48 mmol) is added, and stirring is carried out for 3 hours at ambient temperature. The reaction mixture is added to ice-water. Extraction is carried out with ethyl acetate, and the organic phase is dried over sodium sulfate and concentrated by evaporation. Chromatography on silica gel is carried out in order to remove by-products (eluant: ethyl acetate/hexane 1:15). After removal of the eluant, 0.3 g of 2-(2-nitrophenyl)-bicyclopropane (65% of theory) is obtained in the form of a brownish liquid (trans:cis ratio: 4.7:1).

EXAMPLE P5

Preparation of 2-(2-aminophenyl)-bicyclopropane

In a hydrogenation reactor, 1 g of 2-(2-nitrophenyl)-bicyclopropane (4.9 mmol, trans:cis ratio: 4.1:1), dissolved in 20 ml of ethanol, is hydrogenated at ambient temperature using 0.1 g of 5% platinum-carbon catalyst. After 2.5 hours and after 101% of the amount of hydrogen theoretically required for the reduction has been taken up, the reaction is stopped. Following filtration of the reaction mixture, the solvent is removed by concentration by evaporation. 0.87 g of 2-(2-aminophenyl)-bicyclopropane (100% of theory) is obtained in the form of a brownish liquid (trans:cis ratio: 4.4:1).

The following compounds of formula I can be prepared according to the above Examples:

TABLE 1

Compounds of formula I (I)

| Comp. No. | $R_1$ | $R_2$ | $R_3$ |
|---|---|---|---|
| A1 | H | H | H |
| A2 | $CH_3$ | H | H |
| A3 | H | $CH_3$ | H |
| A4 | H | H | $CH_3$ |
| A5 | $CH_3$ | $CH_3$ | H |
| A6 | $CH_3$ | H | $CH_3$ |
| A7 | H | $CH_3$ | $CH_3$ |
| A8 | $CH_3$ | $CH_3$ | $CH_3$ |

The starting materials for the process of the present invention are distinguished by ease of availability and good handling properties and are moreover reasonably priced.

A further advantage of the process is that the ratio of trans isomers of formula Ia to cis isomers of formula Ib is significantly higher than described in the prior art; generally, trans:cis ratios of the prepared 2-(2-aminophenyl)-bicyclopropanes of more than 3:1 are achieved.

In accordance with the present process, compounds of formula I can be prepared in simple manner wherein the ratio of compounds of formula Ia (trans) to compounds of formula Ib (cis) is from 3:1 to 5:1.

In the process according to the invention, the trans/cis proportion of the end products of the process, the 2-(2-aminophenyl)-bicyclopropanes of formula I, is determined substantially by the trans/cis proportion of the 2-(2-nitrophenyl)-bicyclopropanes of formula IV formed when Process Step (b) is carried out. An increased proportion of trans remains substantially unchanged after Process Step (c), the reduction of the 2-(2-nitrophenyl)-bicyclopropanes to form the end products of the process, has been carried out.

The process according to the invention allows the trans proportion of compounds of formula I to be substantially increased by a further reaction step which is simple to execute.

In that especially preferred embodiment (bb) of the process according to the invention, the compounds of formula IV obtained according to Process Step (b)

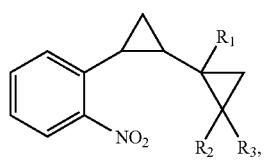

(IV)

wherein $R_1$, $R_2$ and $R_3$ are as defined for formula 1, bb) are isomerised in the presence of a base to form compounds of formula IV wherein the ratio of compounds of formula IVa (trans) to compounds of formula IVb (cis) is more than 6:1. Those compounds are then used in Process Step c).

The increased proportion of trans remains substantially unchanged after Process Step (c) has been carried out. That especially preferred process variant therefore yields compounds of formula I wherein the ratio of compounds of formula Ia (trans) to compounds of formula Ib (cis) is more than 6:1.

Process Step bb):

A suitable base for Process Step bb) is, for example, KOH or an alkali metal or alkaline earth metal alcoholate, such as, for example, a lithium, sodium or potassium alcoholate, especially a methanolate, ethanolate or butanolate. Special preference is given to KOH or potassium tert-butanolate, and very special preference is given to potassium tert-butanolate.

Suitable amounts of base for that reaction are, for example, from 0.3 to 3 equivalents, especially from 0.5 to 1.2 equivalents.

The reaction is preferably carried out in the presence of an inert solvent. Suitable solvents are, for example, aprotic solvents, such as tetrahydrofuran, dimethyl sulfoxide, dimethylacetamide; dimethoxyethane; dioxane or dimethylformamide, and also mixtures thereof; tetrahydrofuran is especially preferred.

In an embodiment to which very special preference is given, that reaction is carried out using potassium tert-butanolate as base and using tetrahydrofuran as solvent.

In another embodiment to which very special preference is given, that reaction is carried out using KOH as base and using dimethyl sulfoxide as solvent.

Temperatures are generally from −20° C. to 80° C., with a range from −20° C. to 25° C. being preferred; special preference is given to carrying out the reaction at ambient temperature.

The reaction time for that reaction is generally from 0.5 to 12 hours, preferably from 1 to 3 hours.

Special preference is given to carrying out that reaction under a nitrogen atmosphere.

By selecting suitable reaction conditions, the compound of formula IV obtained in Reaction Step b) can be isomerised directly, without isolation of intermediates, to form a compound of formula IV wherein the ratio of compounds of formula IVa (trans) to compounds of formula IVb (cis) is more than 6:1 ("one-pot" method). That reaction procedure is a particular advantage of the especially preferred embodiment (bb) of the process according to the invention.

When that especially preferred embodiment (bb) of the process according to the invention is carried out as a "one-pot" method, the solvent used is more especially dimethyl sulfoxide or dimethylformamide.

The above-described especially preferred embodiment (bb) of the process according to the invention is explained in greater detail by way of the following Examples:

EXAMPLE P6

Isomerisation of 2-(2-nitrophenyl)-bicyclopropane

Under a nitrogen atmosphere, 0.5 g of potassium tert-butanolate (4.4 mmol) is added to a solution of 3 g of 2-(2-nitrophenyl)-bicyclopropane (14.7 mmol, trans:cis ratio: 3.7:1) in 100 ml of tetrahydrofuran. The resulting mixture is stirred for 1.5 hours at ambient temperature. Water is added and the reaction mixture is extracted with ethyl acetate. The organic phase is washed with a saturated sodium chloride solution and dried over sodium sulfate and concentrated by evaporation. Chromatography on silica gel is carried out in order to remove by-products (eluant: ethyl acetate/hexane 1:10). After removal of the eluant, 2.35 g of 2-(2-nitrophenyl)-bicyclopropane (91% of theory) are obtained in the form of a yellowish liquid (trans:cis ratio: 6.4:1).

EXAMPLE P7

Isomerisation of 2-(2-nitrophenyl)-bicyclopropane

Under a nitrogen atmosphere, 1.82 g of potassium tert-butanolate (16.1 mmol) are added to a solution of 3 g of 2-(2-nitrophenyl)-bicyclopropane (14.7 mmol, trans:cis ratio: 3.7:1) in 100 ml of tetrahydrofuran. The resulting mixture is stirred for 0.5 hours at −20° C. Water is added and the reaction mixture is extracted with ethyl acetate. The organic phase is washed with a saturated sodium chloride solution and dried over sodium sulfate and concentrated by evaporation. Chromatography on silica gel is carried out in order to remove by-products (eluant: ethyl acetate/hexane 1:10). After removal of the eluant, 2.19 g of 2-(2-nitrophenyl)-bicyclopropane (73% of theory) are obtained in the form of a yellowish liquid (trans:cis ratio: 14.3:1).

EXAMPLE P8

Preparation and Isomerisation of 2-(2-nitrophenyl)-bicyclopropane ("One-Pot" Method)

1.18 g of 1-cyclopropyl-3-(2-nitrophenyl)-propyl methanesulfonate (3.94 mmol) is dissolved in 40 ml of dimethylformamide, 0.91 g of potassium tert-butanolate (97%, 7.88 mmol) are added and stirring is carried out for 1 hour at ambient temperature under a nitrogen atmosphere. Water is added to the reaction mixture. Extraction is carried out with ethyl acetate, and the organic phase is dried over sodium sulfate and concentrated by evaporation. Chromatography on silica gel is carried out in order to remove by-products (eluant: ethyl acetate/hexane 1:2). After removal of the eluant, 0.68 g of 2-(2-nitrophenyl)-bicyclopropane (85% of theory) is obtained in the form of an orange-coloured liquid (trans:cis ratio: 6.5:1).

EXAMPLE P9

Preparation and Isomerisation of 2-(2-nitrophenyl)-bicyclopropane ("one-pot" Method)

1.06 g of 1-cyclopropyl-3-(2-nitrophenyl)-propyl methanesulfonate (3.54 mmol) is dissolved in 20 ml of dimethyl sulfoxide, 1.05 g of potassium tert-butanolate (97%, 10.62 mmol) are added, and stirring is carried out for 1.5 hours at ambient temperature under a nitrogen atmosphere. Water is added to the reaction mixture. Extraction is carried out with ethyl acetate, and the organic phase is dried over sodium sulfate and concentrated by evaporation. Chromatography on silica gel is carried out in order to remove by-products (eluant: ethyl acetate/hexane 1:10). After removal of the eluant, 0.68 g of 2-(2-nitrophenyl)-bicyclopropane (67% of theory) are obtained in the form of an orange-coloured liquid (trans:cis ratio: 7.7:1).

The compounds of formula III

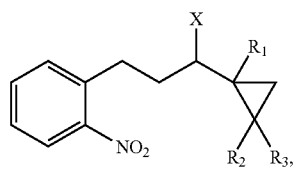
(III)

wherein X is bromine, chlorine or $OSO_2R$, wherein R is $C_1$-$C_4$alkyl, $C_1$-$C_4$fluoroalkyl, benzyl, phenyl, nitrophenyl, halophenyl or $C_1$-$C_6$alkylphenyl and $R_1$, $R_2$ and $R_3$ are as defined for formula I, are valuable intermediates in the preparation of compounds of formula I and were developed specifically for the present process according to the invention. The present invention accordingly relates also to those compounds.

Especially valuable for the preparation of compounds of formula I are those compounds of formula III wherein X is $OSO_2CH_3$.

An intermediate especially suitable for the preparation of compounds of formula I is the compound of formula III wherein X is $OSO_2CH_3$ and $R_1$, $R_2$ and $R_3$ are hydrogen.

Preferred compounds of formula III are listed in the following Table. In the following Table, "Ph" denotes phenyl.

TABLE 2

Compounds of formula III

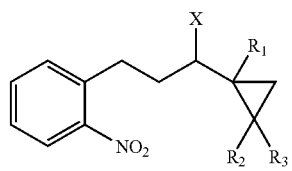
(III)

| Comp. No. | $R_1$ | $R_2$ | $R_3$ | X |
|---|---|---|---|---|
| Z1.01 | H | H | H | $OSO_2CH_3$ |
| Z1.02 | $CH_3$ | H | H | $OSO_2CH_3$ |
| Z1.03 | H | $CH_3$ | H | $OSO_2CH_3$ |
| Z1.04 | H | H | $CH_3$ | $OSO_2CH_3$ |
| Z1.05 | $CH_3$ | $CH_3$ | H | $OSO_2CH_3$ |
| Z1.06 | $CH_3$ | H | $CH_3$ | $OSO_2CH_3$ |
| Z1.07 | H | $CH_3$ | $CH_3$ | $OSO_2CH_3$ |
| Z1.08 | $CH_3$ | $CH_3$ | $CH_3$ | $OSO_2CH_3$ |
| Z1.09 | H | H | H | $OSO_2CH_2Ph$ |
| Z1.10 | $CH_3$ | H | H | $OSO_2CH_2Ph$ |
| Z1.11 | H | $CH_3$ | H | $OSO_2CH_2Ph$ |
| Z1.12 | H | H | $CH_3$ | $OSO_2CH_2Ph$ |
| Z1.13 | $CH_3$ | $CH_3$ | H | $OSO_2CH_2Ph$ |
| Z1.14 | $CH_3$ | H | $CH_3$ | $OSO_2CH_2Ph$ |
| Z1.15 | H | $CH_3$ | $CH_3$ | $OSO_2CH_2Ph$ |
| Z1.16 | $CH_3$ | $CH_3$ | $CH_3$ | $OSO_2CH_2Ph$ |
| Z1.17 | H | H | H | Br |
| Z1.18 | $CH_3$ | H | H | Br |
| Z1.19 | H | $CH_3$ | H | Br |
| Z1.20 | H | H | $CH_3$ | Br |
| Z1.21 | $CH_3$ | $CH_3$ | H | Br |
| Z1.22 | $CH_3$ | H | $CH_3$ | Br |

TABLE 2-continued

Compounds of formula III

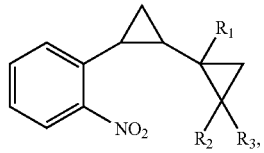
(III)

| Comp. No. | $R_1$ | $R_2$ | $R_3$ | X |
|---|---|---|---|---|
| Z1.23 | H | $CH_3$ | $CH_3$ | Br |
| Z1.24 | $CH_3$ | $CH_3$ | $CH_3$ | Br |
| Z1.25 | H | H | H | Cl |
| Z1.26 | $CH_3$ | H | H | Cl |
| Z1.27 | H | $CH_3$ | H | Cl |
| Z1.28 | H | H | $CH_3$ | Cl |
| Z1.29 | $CH_3$ | $CH_3$ | H | Cl |
| Z1.30 | $CH_3$ | H | $CH_3$ | Cl |
| Z1.31 | H | $CH_3$ | $CH_3$ | Cl |
| Z1.32 | $CH_3$ | $CH_3$ | $CH_3$ | Cl |

The compounds of formula IV

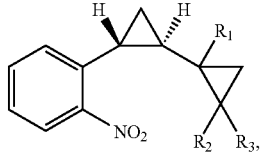
(IV)

wherein $R_1$, $R_2$ and $R_3$ are as defined for formula I and wherein the ratio of compounds of formula IVa (trans)

(IVa, trans)

wherein $R_1$, $R_2$ and $R_3$ are as defined for formula I, to compounds of formula IVb (cis)

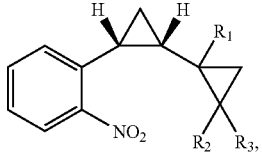
(IVb, cis)

wherein $R_1$, $R_2$ and $R_3$ are as defined for formula I, is from 2:1 to 20:1, are valuable intermediates in the preparation of compounds of formula I and were developed specifically for the present process according to the invention. The present invention accordingly relates also to those compounds.

Especially valuable for the preparation of compounds of formula I are those compounds of formula IV wherein the ratio of compounds of formula IVa (trans) to compounds of formula IVb (cis) is from 6:1 to 20:1, especially from 6:1 to 15:1.

As intermediates for the preparation of compounds of formula I there are especially suitable compounds of formula IV wherein $R_1$, $R_2$ and $R_3$ are hydrogen.

Preferred compounds of formula IV are listed in the following Table:

TABLE 3

Compounds of formula IV

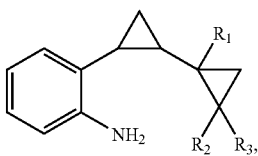

(IV)

| Comp. No. | $R_1$ | $R_2$ | $R_3$ |
|---|---|---|---|
| Z1.1 | H | H | H |
| Z1.2 | $CH_3$ | H | H |
| Z1.3 | H | $CH_3$ | H |
| Z1.4 | H | H | $CH_3$ |
| Z1.5 | $CH_3$ | $CH_3$ | H |
| Z1.6 | $CH_3$ | H | $CH_3$ |
| Z1.7 | H | $CH_3$ | $CH_3$ |
| Z1.8 | $CH_3$ | $CH_3$ | $CH_3$ |

Waht is claimed is:

1. A process for the preparation of a compound of formula I

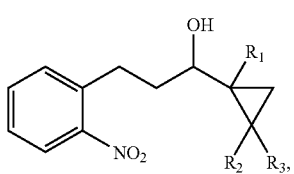

(I)

wherein $R_1$, $R_2$ and $R_3$ are each independently of the others hydrogen or methyl, which comprises
  a) reaction of a compound of formula II

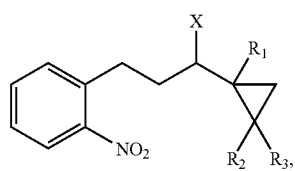

(II)

wherein $R_1$, $R_2$ and $R_3$ are as defined for formula I, either
  a1) with triphenylphosphine dibromide or triphenylphosphine dichloride or
  a2) with $RSO_2Cl$, wherein R is $C_1$-$C_4$alkyl, $C_1$-$C_4$fluoroalkyl, benzyl, phenyl, nitrophenyl, halophenyl or $C_1$-$C_6$alkylphenyl, in the presence of a base,
to form a compound of formula III

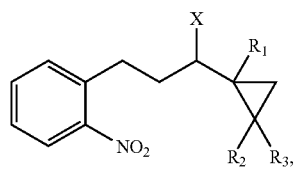

(III)

wherein X is $OSO_2R$, wherein R is $C_1$-$C_4$alkyl, $C_1$-$C_4$fluoroalkyl, benzyl, phenyl, nitrophenyl, halophenyl or $C_1$-$C_6$alkylphenyl, or is bromine or chlorine and $R_1$, $R_2$ and $R_3$ are as defined for formula I; and b) reaction of that compound in the presence of a base to form a compound of formula IV

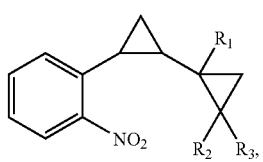

(IV)

wherein $R_1$, $R_2$ and $R_3$ are as defined for formula 1; and
  c) conversion of that compound in the presence of a reducing agent into a compound of formula I.

2. A process according to claim 1, which comprises, after carrying out Process Step b) and before carrying out Process Step c), isomerisation of the compound of formula IV

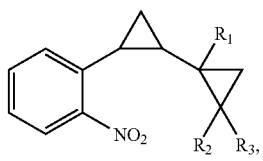

(IV)

wherein $R_1$, $R_2$ and $R_3$ are as defined for formula I in claim 1,
  bb) in the presence of a base to form a compound of formula IV wherein the ratio of the compound of formula IVa (trans)

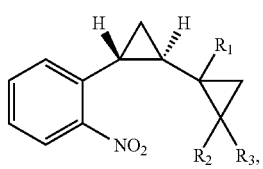

(IVa, trans)

wherein $R_1$, $R_2$ and $R_3$ are as defined for formula I in claim 1, to the compound of formula IVb (cis)

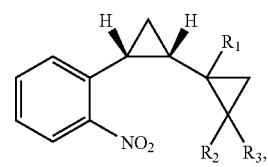

(IVb, cis)

wherein $R_1$, $R_2$ and $R_3$ are as defined for formula I in claim 1, is more than 6:1.

3. A compound of formula III

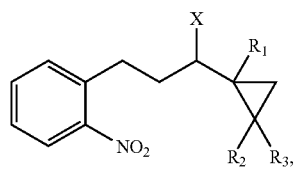

(III)

wherein $R_1$, $R_2$ and $R_3$ are each independently of the others hydrogen or methyl and X is $OSO_2R$, wherein R is $C_1$-$C_4$alkyl, $C_1$-$C_4$fluoroalkyl, benzyl, phenyl, nitrophenyl, halophenyl or $C_1$-$C_6$alkylphenyl, or is bromide or chlorine.

* * * * *